(12) United States Patent
Mengden et al.

(10) Patent No.: US 11,992,336 B2
(45) Date of Patent: May 28, 2024

(54) DEVICE, SYSTEM AND METHOD FOR GENERATING BIOFEEDBACK

(71) Applicants: AIT AUSTRIAN INSTITUTE OF TECHNOLOGY GMBH, Vienna (AT); Thomas Mengden, Dortmund (DE)

(72) Inventors: Thomas Mengden, Dortmund (DE); Siegfried Wassertheurer, Bad Gleichenberg (AT)

(73) Assignees: Thomas Mengden, Dortmund (DE); AIT AUSTRIAN INSTITUTE OF TECHNOLOGY GMBH, Osterreich (AT)

( * ) Notice: Subject to any disclaimer, the term of this patent is extended or adjusted under 35 U.S.C. 154(b) by 652 days.

(21) Appl. No.: 16/474,857

(22) PCT Filed: Dec. 21, 2017

(86) PCT No.: PCT/EP2017/083976
§ 371 (c)(1),
(2) Date: Jun. 28, 2019

(87) PCT Pub. No.: WO2018/122082
PCT Pub. Date: Jul. 5, 2018

(65) Prior Publication Data
US 2021/0000412 A1    Jan. 7, 2021

(30) Foreign Application Priority Data
Dec. 29, 2016    (DE) .............. 10 2016 015 631.7

(51) Int. Cl.
*A61B 5/00*    (2006.01)
*A61B 5/02*    (2006.01)
(Continued)

(52) U.S. Cl.
CPC .......... *A61B 5/486* (2013.01); *A61B 5/02028* (2013.01); *A61B 5/02125* (2013.01);
(Continued)

(58) Field of Classification Search
CPC . A61B 5/486; A61B 5/02028; A61B 5/02125; A61B 5/02405; A61B 5/029;
(Continued)

(56) References Cited

U.S. PATENT DOCUMENTS 6,554,763 B1    4/2003    Amano et al.
7,177,686 B1 *    2/2007    Turcott .............. A61N 1/36585
                                                                607/23
(Continued)

FOREIGN PATENT DOCUMENTS

DE    10 2005 003 678    8/2006
DE    10319361 A1    12/2014
(Continued)

OTHER PUBLICATIONS

F. B. Reguig, "Photoplethysmogram signal analysis for detecting vital physiological parameters: An evaluating study," 2016 International Symposium on Signal, Image, Video and Communications (ISIVC), 2016, pp. 167-173, doi: 10.1109/ISIVC.2016.7893981. (Year: 2016).*

(Continued)

*Primary Examiner* — Yi-Shan Yang
*Assistant Examiner* — Kyle W. Kretzer
(74) *Attorney, Agent, or Firm* — Branch Partners PLLC; Bruce E. Black

(57) ABSTRACT

An apparatus for generating biofeedback, in particular during a relaxation exercise for lowering blood pressure, comprises at least one interface for receiving a pulse wave signal that represents a pressure pulse or volume pulse of a pulse wave in a blood circulation system as a function of time and (Continued)

an ECG signal. The apparatus comprises an evaluation device that is configured to determine a pulse transit time on the basis of the pulse wave signal and the ECG signal, perform an evaluation of a pulse wave form of the pulse wave signal and generate the biofeedback depending on the pulse transit time and/or the evaluation of the pulse wave form. The apparatus comprises an output interface for providing the biofeedback.

20 Claims, 9 Drawing Sheets

(51) Int. Cl.
*A61B 5/021* (2006.01)
*A61B 5/024* (2006.01)
*A61B 5/029* (2006.01)
*A61B 5/318* (2021.01)

(52) U.S. Cl.
CPC .......... *A61B 5/02405* (2013.01); *A61B 5/029* (2013.01); *A61B 5/318* (2021.01); *A61B 5/4035* (2013.01); *A61B 5/4836* (2013.01); *A61B 5/7239* (2013.01); *A61B 5/742* (2013.01)

(58) Field of Classification Search
CPC ....... A61B 5/318; A61B 5/4836; A61B 5/742; A61B 5/0261; A61B 5/4035; A61B 5/7239; A61B 5/349; A61B 5/0816
See application file for complete search history.

(56) References Cited

U.S. PATENT DOCUMENTS

| | | |
|---|---|---|
| 2003/0036685 A1 | 2/2003 | Goodman |
| 2004/0116784 A1 | 6/2004 | Gavish |
| 2007/0056582 A1* | 3/2007 | Wood .................. A61B 5/0245 128/200.24 |
| 2009/0216132 A1* | 8/2009 | Orbach ................ A61B 5/7445 600/485 |
| 2014/0275888 A1* | 9/2014 | Wegerich ............... A61B 5/053 600/324 |
| 2017/0238818 A1* | 8/2017 | Gaurav ................ A61B 5/7264 |
| 2018/0333056 A1* | 11/2018 | Chou ................ A61B 5/02438 |

FOREIGN PATENT DOCUMENTS

| | | |
|---|---|---|
| WO | 00/51677 | 9/2000 |
| WO | 2006/100676 | 9/2006 |
| WO | 2008/128531 | 10/2008 |
| WO | 2009/112000 | 9/2009 |

OTHER PUBLICATIONS

International Search Report and Written Opinion for PCT Application No. PCTIEP2017/083976 mailed Mar. 23, 2018.
Reguig F Bereksi: "Photoplethysmogram signal analysis for detecting vital physiological parameters: An evaluating study", 2016 International Symposium on Signal, Image, Video and Communications (ISNC), IEEE, Nov. 21, 2016 (Nov. 21, 2016), pp. 167-173, XP033084496, DOI: 10.1109/ISNC.2016.7893981 [retrieved on Apr. 6, 2017].

* cited by examiner

DEVICE, SYSTEM AND METHOD FOR GENERATING BIOFEEDBACK

CROSS-REFERENCE TO RELATED APPLICATIONS

This present application is a U.S. national stage application PCT Application No. PCT/EP2017/083976, filed Dec. 21, 2017 which claims priority to German Patent Application No. 10 2016 015 631.7 filed Dec. 29, 2016 both of which are hereby incorporated by reference in their entireties.

The invention relates to apparatuses, systems and methods for generating biofeedback. The invention in particular relates to apparatuses, systems and methods which can provide information on changes in vital signs during an exercise in order to make the effectiveness of the exercise recognizable to a user.

Hypertension is a significant health risk that may have various causes. Chronic stress levels may play an important role in the development of essential arterial hypertension, since they may lead to a shift in the vegetative balance between the sympathetic nervous system and the parasympathetic nervous system. Such a shift in the vegetative balance may affect various organs, such as, for example, the cardiovascular system, and may lead to an increase in heart rate, an increase in ventricular contraction and a narrowing of the peripheral vessels. Initially acutely and temporarily, but later also chronically, such a condition may lead to an increase in blood pressure, which increases the risk of consequences such as stroke, heart failure and kidney failure.

Non-invasive techniques for lowering blood pressure are attractive. Breathing techniques such as mantra breathing are examples of relaxation techniques that may be used to alleviate at least certain mild forms of arterial hypertension. Yoga or other relaxation techniques may also be used to influence blood pressure. It is desirable to give feedback on the effectiveness of a relaxation technique to the person performing it. This allows the correct execution to be checked and motivation to be increased. Conventionally, a heart rate variability (HRV) derived from an electrocardiogram (ECG) signal is used and output as a surrogate parameter since it can be easily detected. With such conventional systems, however, it has not been possible so far to output the acute effects on blood pressure as biofeedback. However, changes in HRV do not necessarily have to be accompanied by changes in blood pressure. During a relaxation exercise, for example, these changes in blood pressure may only occur with a considerable delay compared to a change in heart rate or pulse rate.

When a cuff-type blood pressure meter is used, the blood pressure can be detected and output as biofeedback. An exemplary system using a cuff-type blood pressure meter is described in DE 10 2010 014 761 A1. However, the use of a cuff-type blood pressure meter may be perceived as disturbing by users and may detract from the effectiveness of the relaxation exercise.

Changes in blood pressure lead to changes in the pulse transit time (PTT) and pulse wave velocity (PWV) of pressure pulses or volume pulses in the blood circulation system due to a changed transmural wall tension of the arteries. With increasing blood pressure values, the pulse wave velocity increases and the pulse transit time therefore decreases. Decreasing blood pressure values lead to an increase in pulse transit time. The pulse transit time may be used as a parameter that indicates a change in blood pressure. Exemplary systems which allow the measurement of the pulse transit time are described in DE 10 2005 003 678 A1 and DE 10 2010 014 761 A1. However, the biofeedback provided by such systems can only provide limited information on the effectiveness of a relaxation exercise, since it is not possible to determine, for example, the mode of action in the body that causes a detected change in blood pressure.

WO 2009/112000 A1 discloses an apparatus for determining cardiovascular variability that uses non-invasively recorded blood pressure signals for analysis. This apparatus is used for clinical analysis of recorded signals and is not configured to provide biofeedback.

The object underlying the present invention resides in providing apparatuses, systems and methods that offer improvements with respect to at least some of the aforementioned disadvantages of conventional systems. In particular, the object to be achieved with the present invention is to provide apparatuses, systems and methods which, during the performance of a relaxation exercise, can derive additional information which may be relevant to the effectiveness of the relaxation exercise.

According to the invention, an apparatus, system and method with the features defined in the independent claims are provided. The dependent claims define embodiments.

An apparatus for generating biofeedback according to the invention comprises at least one interface for receiving a pulse wave signal that represents a pressure pulse or volume pulse of a pulse wave in a blood circulation system as a function of time and an ECG signal. The apparatus comprises an evaluation device that is configured to determine a pulse transit time on the basis of the pulse wave signal and the ECG signal and/or to perform an evaluation of a pulse wave form of the pulse wave signal and to generate the biofeedback depending on the pulse transit time and/or the evaluation of the pulse wave form. The apparatus comprises an output interface for providing the biofeedback.

The apparatus may be configured such that during operation it not only determines a pulse transit time, which allows changes in blood pressure to be detected, but can also perform an evaluation of the pulse wave form of the detected pressure pulse or volume pulse. More meaningful biofeedback can thus be provided to the user. Typical hemodynamic changes can be detected by means of analyzing the pulse wave form. Based on changes in peaks of the pulse wave form, the apparatus can automatically draw conclusions on whether only cardiac pumping capacity and heart rate have changed, for example, or whether additionally the peripheral resistance of vessels has been reduced.

The pulse transit time is inversely proportional to the pulse wave velocity. Accordingly, information about the pulse wave velocity is also determined by detecting the pulse transit time. The generation of biofeedback depending on the pulse transit time can be performed in different ways, wherein in particular the determination of a pulse wave velocity on the basis of the pulse transit time and a further evaluation of the pulse wave velocity are also included.

Due to the relationship between the pulse transit time and the pulse wave velocity, reference is subsequently made only to the pulse transit time, wherein it is understood that a dependence of biofeedback on the pulse transit time in the sense of this application also implies a dependence of biofeedback on the pulse wave velocity, and that a dependence of a physiological variable on the pulse transit time in the sense of this application also implies a dependence of the physiological variable on the pulse wave velocity.

The evaluation device may be configured to determine a mode of action underlying a change in blood pressure, a magnitude of the change in blood pressure, a change in cardiac pumping capacity and/or a change in pulse wave reflection by evaluating the pulse wave form. To this end, the evaluation device can, for example, determine how the position and/or height of peaks of the pulse wave signal changes with increasing duration of the relaxation exercise by means of several detected pressure pulses or volume pulses. Typical hemodynamic changes can be detected in this way without the use of, for example, a cuff-type blood pressure meter being mandatory.

The evaluation device may be configured to determine whether there is a change in blood pressure caused by vagus enhancement or sympathetic attenuation by evaluating the pulse wave form. For example, it may be desirable to induce a change in blood pressure specifically by activating the parasympathetic nervous system (vagus activation) to improve the vegetative balance or by sympathetic attenuation to reduce peripheral resistance. Accordingly, the apparatus can detect the mode of action underlying the change in blood pressure, for example by automatically differentiating between vagus activation and sympathetic attenuation, and can provide respective biofeedback.

The evaluation device may be configured to indicate via the output interface whether there is a change in blood pressure caused by vagus enhancement or sympathetic attenuation. In this way, meaningful biofeedback can be provided to a user who, for example, aims at lowering blood pressure through sympathetic attenuation in order to reduce peripheral resistance.

The evaluation device may be configured to detect a change in at least one of the following variables in order to determine whether there is a change in blood pressure caused by vagus enhancement or sympathetic attenuation: duration of an early systolic phase; pressure in the early systolic phase; and/or duration of a late systolic phase. Changes in these variables can be easily detected, for example from heartbeat to heartbeat. By comparing these variables for several cardiac cycles, it can be determined whether the peripheral resistance of the vessels is reduced if the late systolic phase is extended. A comparison of these variables for several cardiac cycles can also reveal a change in cardiac pumping capacity.

The evaluation device may be configured to perform the determination of the pulse transit time and/or the evaluation of the pulse wave form for each cardiac cycle of a plurality of successive cardiac cycles. This allows a time-resolved detection per heartbeat of how the transit time of the pressure pulse or volume pulse changes from the heart until its detection by a sensor as well as how the transit time of the pressure pulse or volume pulse reflected by the peripheral vessels changes.

The apparatus may be configured to output the respective biofeedback via the output interface for each cardiac cycle of the plurality of successive cardiac cycles. This allows time-resolved biofeedback to be provided to the user.

The biofeedback may include at least one piece of information selected from the group consisting of: change in blood pressure, blood pressure, cardiac pumping capacity, pulse wave reflection and mode of action underlying the change in blood pressure. This information allows the user to check the effectiveness of the relaxation exercise for lowering blood pressure, for example by vagus activation or sympathetic attenuation.

The apparatus may be configured to output both the biofeedback and instructions for performing the relaxation exercise, in particular breathing instructions, via the output interface. Thus, the user can be guided to perform the relaxation exercise with only one apparatus, which, for example, may be configured as a handheld apparatus, and can evaluate the effectiveness on the basis of the biofeedback.

The apparatus may be configured to generate the instructions for performing the relaxation exercise depending on the pulse transit time and/or the evaluation of the pulse wave form. Thereby, the behavior of the user can be influenced in a targeted way in a kind of feedback loop during the relaxation exercise.

The output interface may comprise an optical output unit. The apparatus may be configured to output the instructions for performing the relaxation exercise and the biofeedback at the same time via the optical output unit. The optical output unit can be, for example, a screen of a handheld apparatus. Thus, an impression of the effectiveness of the relaxation exercise can be graphically given to the user. The output interface may alternatively or additionally comprise an acoustic output unit, for example a loudspeaker.

The evaluation device may be configured to determine the pulse transit time and/or at least one characteristic of the pulse wave form determined by the evaluation of the pulse wave form as a function of a parameter of the relaxation exercise, in particular a breathing rate. This allows the execution of the relaxation exercise to be correlated with the resulting change in vital signs, for example by gradually reducing the breathing rate during mantra breathing.

The apparatus may be a mobile apparatus, in particular a portable apparatus. The apparatus may be configured as a handheld apparatus. The apparatus may be a portable communication device having a communication interface for communication with a wide area network or a cellular communication network. The apparatus may be a cell phone, a tablet computer or a portable computer in order to receive signals from sensors and in order to determine the pulse transit time as well as evaluate the pulse wave form.

A system according to the invention comprises the apparatus for generating biofeedback according to an exemplary embodiment. The system comprises a sensor device which may be coupled to the at least one interface of the apparatus and which is configured to detect the pulse wave signal.

The sensor device may comprise a first sensor for detecting the pulse wave signal and a second sensor for detecting the ECG signal. The first sensor may be configured to detect the pulse wave signal by infrared light transmission or infrared light reflection. The first sensor may comprise a photoplethysmography device. The first sensor may be configured to be reversibly detachably attached to a finger, wrist or arm, for example.

The first sensor may be configured to transmit the pulse wave signal in data packets or data frames to the apparatus. The first sensor may comprise an interface for wired or wireless packaged data transmission to transmit the pulse wave signal to the apparatus. Similarly, the second sensor may be configured to transmit the ECG signal in data packets or data frames to the apparatus. The second sensor may comprise an interface for wired or wireless packaged data transmission to transmit the ECG signal to the apparatus.

The system may comprise a controller for controlling the first sensor and the second sensor and for synchronizing the pulse wave signal detected by the first sensor and the ECG signal detected by the second sensor.

A method for generating biofeedback, in particular during a relaxation exercise for lowering blood pressure, comprises the following steps: receiving a pulse wave signal representing a pressure pulse or volume pulse of a pulse wave in a blood circulation system as a function of time and receiving an ECG signal at an interface; determining a pulse transit time by evaluating the pulse wave signal and the ECG signal and/or evaluating a pulse wave form of the pulse wave signal; generating the biofeedback depending on the pulse transit time and/or the evaluation of the pulse wave form; and outputting the biofeedback.

The method not only determines a pulse transit time, which allows changes in blood pressure to be detected, but also performs an evaluation of the pulse wave form of the detected pressure pulse or volume pulse. More meaningful biofeedback can thus be provided to the user. Typical hemodynamic changes can be detected by means of analyzing the pulse wave form. Based on changes in the peaks of the pulse wave form, the apparatus can automatically draw conclusions on whether only cardiac pumping capacity and heart rate have changed, for example, or whether additionally the peripheral resistance of vessels has been reduced.

The biofeedback can be generated during a guided relaxation exercise for lowering blood pressure, especially during a breathing exercise.

It can be determined whether a change in blood pressure is caused by vagus enhancement or sympathetic attenuation by evaluating the pulse wave form. The output biofeedback can indicate whether the change in blood pressure is caused by vagus enhancement or sympathetic attenuation.

The method can be carried out by the apparatus or the system according to an exemplary embodiment.

Further optional features of the method and the respective effects achieved thereby correspond to the features and effects described with reference to exemplary embodiments of the apparatus.

Preferred embodiments of the invention are described in detail below with reference to the Figures, in which FIG. 1 shows a schematic illustration of a system according to an exemplary embodiment;

In the following, preferred and advantageous exemplary embodiments of the invention are described with reference to the Figures, in which identical reference signs designate identical or similar elements. The features of the various exemplary embodiments may be combined with each other, unless this is expressly excluded in the following description.

Figure 1:
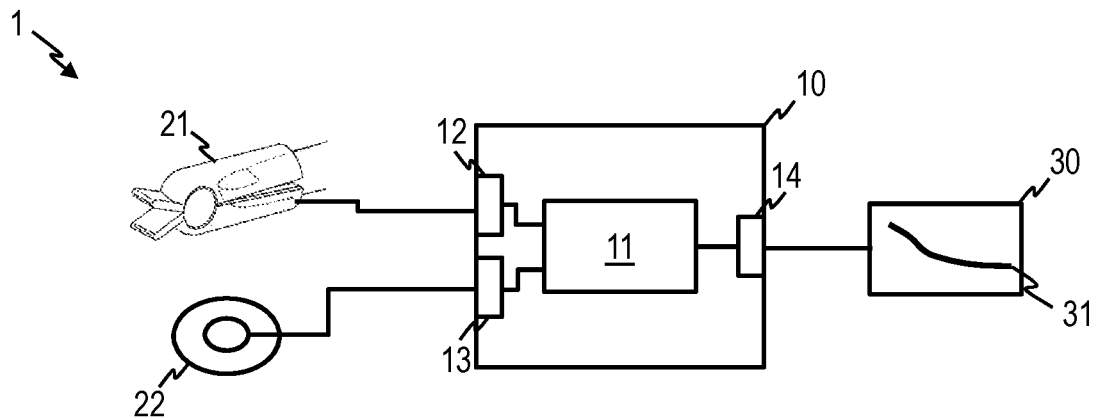

FIG. 1 shows a schematic illustration of a system 1 according to an exemplary embodiment. The system 1 comprises one or more sensors 21, 22 for detecting a pulse wave signal and an ECG signal. The system 1 comprises an apparatus 10 for generating biofeedback. The apparatus 10 can be configured in such a way that it determines a pulse transit time of a pressure pulse or volume pulse in the blood circulation system from the pulse wave signal and the ECG signal and additionally evaluates a pulse wave form of the pulse wave signal in order to generate biofeedback. The apparatus 10 can output the biofeedback via an optical output unit 30 structurally integrated into the apparatus 10 or separate therefrom.

The sensors 21, 22 may be configured for non-destructively reversibly detachable attachment to a human body. The sensors 21, 22 may use different measuring techniques for detecting the pulse wave signal and the ECG signal. Such measuring techniques are known to the person skilled in the art and are therefore not described in detail here. The sensor 21 may comprise, for example, a photoplethysmography device for detecting a pressure pulse or volume pulse of a pulse wave in a blood circulation system. The sensor 21 for detecting the pressure or volume pulse may be configured for detachable attachment to a finger. The sensor 21 for detecting the pressure pulse or volume pulse may be configured as a device attachable to the wrist or may be integrated with other sensors in such a device. The sensor 21 for detecting the pressure pulse or volume pulse may also be integrated into a device that has other functions, such as headphones attachable in or on an ear. The sensor 22 for detecting the ECG signal may be integrated into a chest strap or other holder or may comprise an adhesive surface for attachment. The sensors 21, 22 can be coupled via a wired or wireless connection with an apparatus 10 for generating biofeedback.

The apparatus 10 comprises at least one interface 12, 13 for receiving the ECG signal and the pulse wave signal from the sensors 21, 22. The at least one interface 12, 13 may be configured for wired or wireless communication with the sensors 21, 22. The at least one interface 12, 13 can be a USB or Bluetooth interface. The at least one interface 12, 13 may be configured to receive the ECG signal and the pulse wave signal in data packets or data frames, and to synchronize the data transmission and data acquisition between the sensors 21, 22.

The apparatus 10 comprises an evaluation device 11 for evaluating the ECG signal and the pulse wave signal. The evaluation device 11 may comprise at least one integrated semiconductor circuit. The evaluation device 11 may comprise a special application-specific circuit, a controller, a microcontroller, a processor, a microprocessor or any combination of these or other integrated semiconductor circuits.

The evaluation device 11 is configured to evaluate the ECG signal and the pulse wave signal for the generation of biofeedback. The evaluation device 11 is configured to determine a pulse transit time of the pressure pulse or volume pulse from the heart to the sensor 21 on the basis of the ECG signal and the pulse wave signal. The evaluation device 11 is configured to automatically determine further information in addition to the pulse transit time by evaluating a pulse wave form of the pulse wave signal. This additional information may include, for example, a change in cardiac pumping performance during a relaxation exercise that can be determined on the basis of a change in amplitude of pressure pulses or volume pulses during the relaxation exercise. Alternatively or additionally, a change in a peripheral resistance of the blood circulation system can be detected during the relaxation exercise, said change being determinable from a relative position of two peaks of a pressure pulse or volume pulse. Alternatively or additionally, it can be detected whether a change in blood pressure is caused by the sympathetic or parasympathetic nervous system (e.g., vagus). Examples of other information that can be determined from the analysis of the pulse wave form include the change in resistance of peripheral blood vessels or the change in pulse wave reflection in the blood circulation system.

The evaluation device 11 is configured to generate biofeedback and output it via an output interface. The biofeedback can be transmitted, for example, via an interface 14 to an optical display unit 30 and output from this unit. The biofeedback can indicate the change in one or more vital signs during a relaxation exercise as a function of time and/or as a function of a parameter characterizing the performance of the relaxation exercise, such as a breathing rate. The biofeedback may include, but is not limited to, information about a change in blood pressure, cardiac pumping capacity, pulse wave reflection and/or a mode of action underlying the change in blood pressure.

The apparatus 10 may be used to output biofeedback during the performance of a relaxation exercise. The apparatus 10 can generate not only the biofeedback for output via an output interface, but also instructions for performing the relaxation exercise. Breathing instructions are exemplary for such instructions. The instructions for performing the relaxation exercise can be generated depending on the time-dependent change of the pulse transit time and/or depending on the evaluation of the pulse wave form. For example, depending on the evaluation of the pulse wave form, the instructions can be generated in such a way that a change in blood pressure becomes more likely due to sympathetic attenuation or vagus enhancement.

A non-limiting application of the apparatus 10 is described below in the context of mantra breathing, wherein the apparatus 10 is not limited to this application. Deep and slow mantra breathing is a method of lowering blood pressure. Mantra breathing with breathing rates of six breaths per minute leads acutely and chronically to a sensitization of the baroreflex and thus to a reduction in blood pressure. In addition, the parasympathetic nervous system (vagus) is activated, thus improving the vegetative balance. Blood pressure and heart rate can be reduced thereby. As a direct, non-invasive and continuously measurable parameter, the pulse transit time can be determined by the apparatus 10 and output as acute feedback on the change in blood pressure. The change in pulse transit time can be different depending on the user so that, observed in isolation, the change in pulse transit time can be influenced by several temporarily effective factors of the circulation control. By analyzing the pulse wave form of the pulse wave signal, which represents a pressure pulse or volume pulse in the blood circulation system, the apparatus 10 can generate additional and even more meaningful biofeedback. It is possible to detect the effects of various relaxation techniques on blood pressure by means of recording and analyzing the pulse wave form as well as the pulse transit time from the heart to the periphery, for example to a finger. The analysis of the pulse wave form allows a conclusion on the mode of action as well as conclusions about the magnitude of the change in blood pressure to be drawn. The pulse wave form and pulse transit time can be continuously or quasi-continuously recorded and analyzed during the relaxation exercise so that the biofeedback can be updated at each heartbeat.

The determination of the pulse transit time and the analysis of the pulse wave form carried out by the apparatus 10 is described in more detail using exemplary signal forms with reference to FIG. 2 to FIG. 5.

Figure 2:
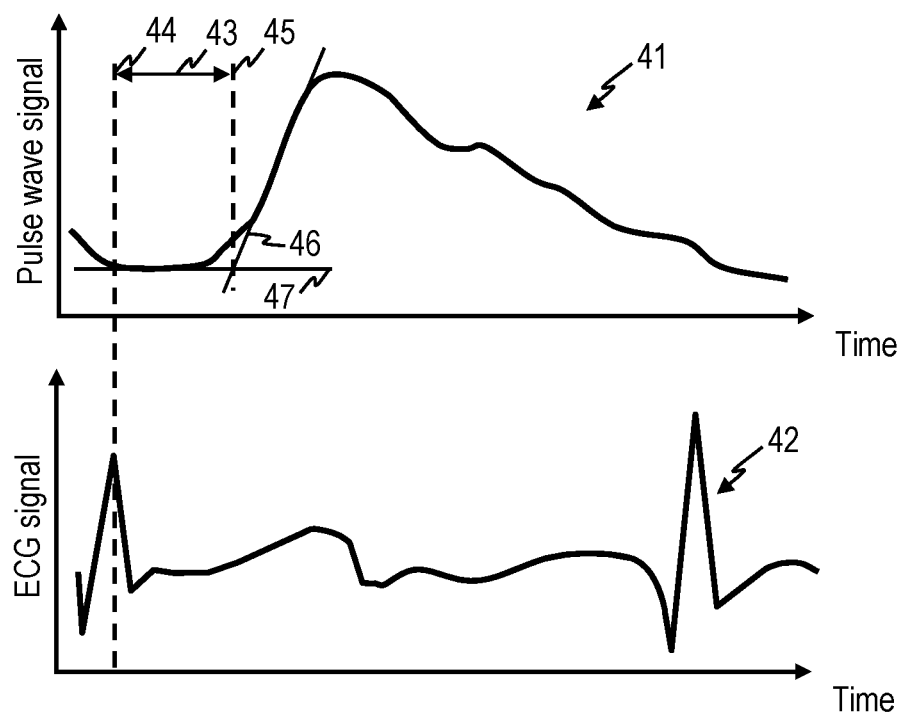
FIG. 2 shows a schematic illustration of a pulse wave signal and an ECG signal for explaining the mode of operation of the apparatus according to an exemplary embodiment.

FIG. 2 shows a schematic illustration of a pulse wave signal 41 and an ECG signal 42. The apparatus 10 may receive the pulse wave signal 41 and the ECG signal 42 from the at least one sensor 21, 22, for example in the form of data packets or data frames. For the purpose of determining the pulse transit time, the apparatus 10 can determine a point in time 44 of an R wave of the ECG signal 42. The R wave of the ECG signal 42 indicates the beginning of the propagation of the pressure pulse or volume pulse in the blood circulation system from the heart. For the purpose of determining the arrival time of the pressure pulse or volume pulse in a part of the blood circulation system where the sensor 21 detects the pressure pulse or volume pulse, the apparatus 10 can determine a point in time at which the rising edge of the pulse wave signal 41 begins. This may be done, for example, by means of a threshold value comparison. In an embodiment, an intersection point between a tangent 46 to the rising edge of the pulse wave signal 41 and a straight line 47 passing through the minimum of the J wave of the pulse wave signal 41 can be determined for the purpose of a more precise determination of the pulse transit time. The point in time 45 corresponding to this intersection point represents the arrival time of the pressure pulse or volume pulse detected by the sensor 21. The pulse transit time 43 can be determined as the time difference between the R wave of the ECG signal 42 and the arrival time of the pressure pulse or volume pulse detected by the sensor 21.

The apparatus 10 can determine the pulse transit time 43 for each of a plurality of pressure pulses or volume pulses triggered by a plurality of sequential heartbeats. The apparatus 10 can determine the pulse transit time 43 individually for each heartbeat during the performance of a relaxation exercise. From heartbeat to heartbeat, the respectively determined pulse transit time or the respective change in blood pressure corresponding thereto, for example relative to the beginning of the relaxation exercise, can be output as biofeedback. Optionally, further processing, for example by calculating a moving average or by filtering out measurement outlier values, can be carried out in order to generate the biofeedback.

Figure 3:
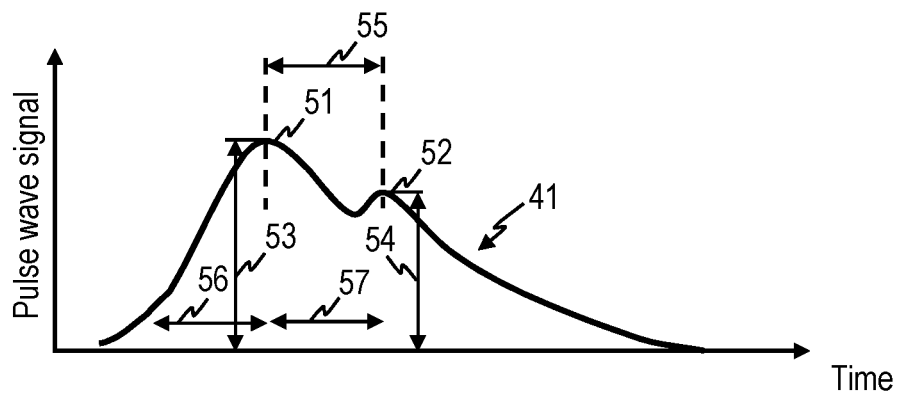
FIG. 3 shows a schematic illustration of a pulse wave form of a pulse wave signal for explaining the mode of operation of the apparatus according to an exemplary embodiment.
Figure 4:
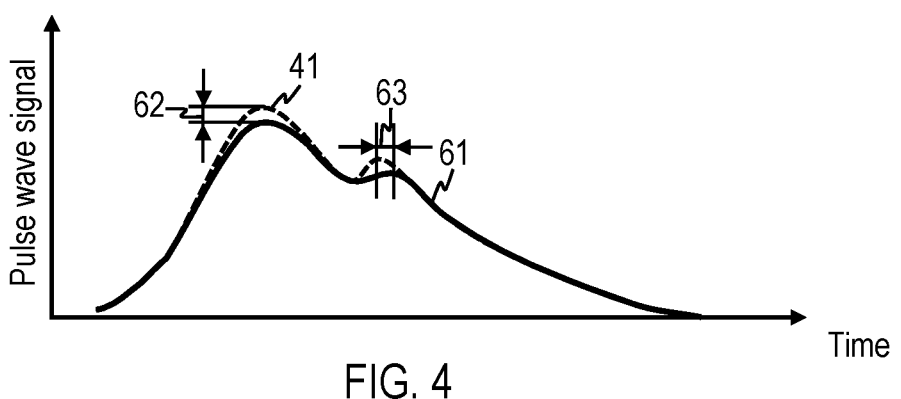
FIG. 4 shows a schematic illustration of a pulse wave form of a pulse wave signal for explaining the mode of operation of the apparatus according to an exemplary embodiment.
Figure 5:
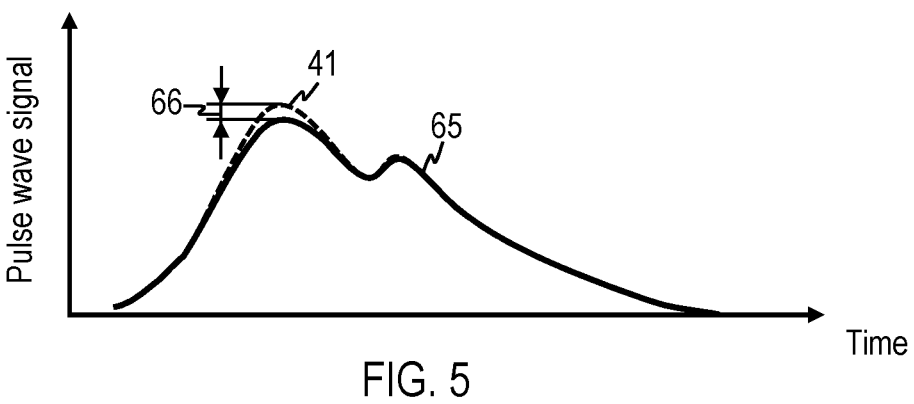
FIG. 5 shows a schematic illustration of a pulse wave form of a pulse wave signal for explaining the mode of operation of the apparatus according to an exemplary embodiment.

FIG. 3, FIG. 4 and FIG. 5 show a schematic illustration of a pulse wave form of a pulse wave signal 41, 61 and 65, respectively. The apparatus 10 can receive the pulse wave signal 41, 61, 65 from the sensor 21, for example in the form of data packets or data frames. The pulse wave signal 41, 61, 65 represents the pressure pulse or volume pulse detected by the sensor 21 as a function of time. What is shown is in each case only the pulse form of the pulse wave signal that corresponds to only one pressure pulse or volume pulse caused by a single heartbeat. The pulse wave form of the pulse wave signal 41, 61, 65 typically comprises a first peak 51 and a second peak 52. The second peak 52 is caused by the reflection of the pressure pulse or volume pulse from the heart in peripheral blood vessels. The pulse wave form depends, for example, on the cardiac pumping capacity and the resistance of peripheral vessels. The cardiac pumping capacity, for example, affects an amplitude 53 of the first peak 51. The resistance of peripheral vessels affects an amplitude 54 of the second peak 52 as well as a time interval 55 between the peaks 51, 52. The duration of an early systole 56 and/or the duration of the late systole 57, for example, can be affected by changing the resistance of vessels.

A change in pulse wave form during a relaxation exercise allows conclusions to be drawn that are suitable for use as biofeedback. For example, an increase in blood pressure caused by the sympathetic nervous system leads to the following changes: increase in peripheral resistance and increase in afterload; increase in cardiac pumping capacity; and increase in heart rate. Accordingly, these hemodynamic changes are also reflected in the pulse wave form and lead to the following changes: shortening of the early systolic phase 56; increase in the pressure in the early systolic phase 56; as well as earlier pulse wave reflection and shortening of the "late" systole 57, which is associated with a change in pulse wave contour in this area. In contrast, an increase in blood pressure caused by the vagus (vagus attenuation) leads to the following changes: increase in heart rate as well as increase in the cardiac pumping capacity.

Thus, the hemodynamic changes induced by the vagus change the pulse wave form in a way different from that of the hemodynamic changes induced by the sympathetic nervous system, since the peripheral resistance and thus the afterload are not affected by the vagus. The late systole is affected only insignificantly by a vagus enhancement or vagus attenuation.

A reduction in blood pressure caused by a relaxation technique such as mantra breathing can be unspecifically identified by an increase in the pulse transit time. In addition, the underlying mechanism can be detected by an additional analysis of the pulse wave contour. In particular, it can be distinguished in this way whether a change in blood pressure is caused by vagus enhancement or sympathetic attenuation. The user can retrieve information via an interface indicating whether a reduction in the resistance of peripheral vessels has been achieved over several relaxation exercises. Such information does not have to be output during the relaxation exercise but can be generated and output, for example, as part of a report created after several exercises for the subject or a specialist taking care of the subject.

FIG. 4 shows a pulse wave form 61 of a pulse wave signal detected during a relaxation exercise during which a sympathetic attenuation has been achieved. With a broken line, the pulse wave form of the pulse wave signal 41 which has been detected at the beginning of the relaxation exercise and can serve as a reference for the analysis of the changes in the pulse wave form is shown as well. In the case of sympathetic attenuation, the decrease in cardiac pumping capacity causes the amplitude 53 of the first peak of the pulse wave signal 61 to be reduced in comparison to the reference signal 41. The corresponding reduction 62 of the peak 51 can also be determined quantitatively by the apparatus 10. In addition, the late systole 57 has been extended since, compared to the reference signal 41, the second peak 52 of the pulse wave signal 61 comprises a shift 63 towards a relatively later time when the pulse wave signals are scaled to the same time duration. In the case of the reduction in blood pressure caused by sympathetic attenuation, the reduction in peripheral resistance and afterload thus leads to a shift 63 of the second peak in the pulse wave form of the pulse wave signal 61.

FIG. 5 shows a pulse wave form 65 of a pulse wave signal detected during a relaxation exercise during which a vagus enhancement has been achieved. With a broken line, the pulse wave form of the pulse wave signal 41 which has been detected at the beginning of the relaxation exercise and can serve as a reference for the analysis of the changes in the pulse wave form is shown as well. In contrast to sympathetic attenuation, the pulse wave form hardly changes in the late systole, since the peripheral resistance and the afterload are not so significantly affected by vagus enhancement.

Both with sympathetic attenuation and with vagus enhancement, the heart rate and thus the duration of the pressure pulse or volume pulse change in addition to the pulse wave form. This has been taken into account in that the pulse wave forms in FIG. 4 and FIG. 5 are shown along the time axis in a manner compressed to the same time period as the pulse wave form 41 used as a reference. The apparatus 10 can also take into account the change in heart rate by way of calculation in that the the duration of each pressure pulse or volume pulse is determined by way of calculation and the pulse wave form is stretched or compressed by a scaling factor along the time axis to facilitate comparability with a reference pulse wave form 41.

The apparatus 10 may be configured to determine a time derivative of the pulse wave signal for the analysis of the pulse wave form. The apparatus 10 can be configured to determine both a first time derivative of the pulse wave signal and a second time derivative of the pulse wave signal. Optionally, the apparatus 10 may be configured to determine at least one first time derivative of the ECG signal for determining the duration of the early systole and/or the duration of the late systole. The duration of the early systole 56 and the duration of the late systole 57 as well as optionally a curvature of the pulse wave signal in the late systole can be reliably determined on the basis of the time derivatives.

Figure 6:
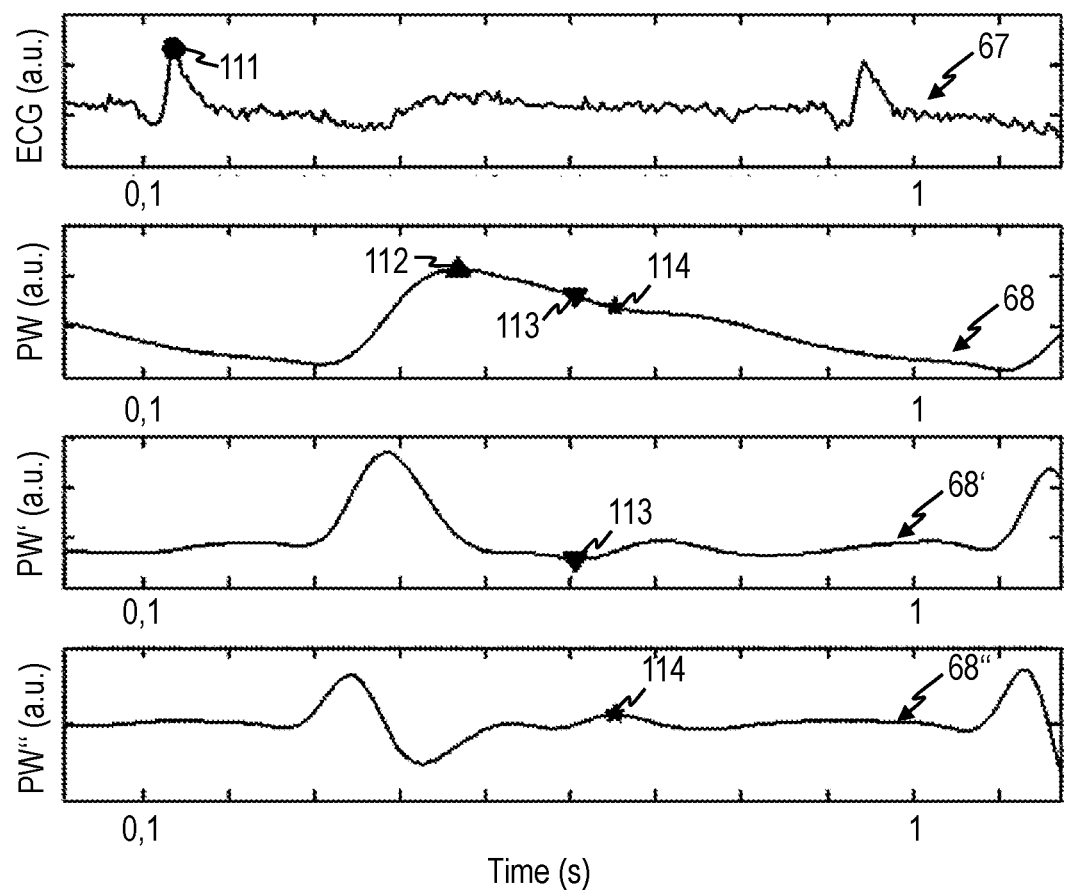
FIG. 6 shows a schematic illustration of signal forms for explaining the mode of operation of the apparatus according to an exemplary embodiment.

FIG. 6 shows an ECG signal 67, a pulse wave signal 68, a first time derivative 68' of the pulse wave signal 68 and a second time derivative 68" of the pulse wave signal 68 for the purpose of further explaining the operation of the apparatus 10. The apparatus 10 may be configured to determine a point in time of an R wave of the ECG signal 67. To this end, a maximum 111 of the ECG signal can be identified, wherein the apparatus 10 optionally determines a first time derivative of the ECG signal. Similarly, a maximum 112 of the pulse wave signal can be automatically identified by the apparatus 10.

The apparatus 10 can determine the end of the systole 113 and the curvature 114 of the pulse wave signal in the late systolic phase on the basis of the first time derivative 68' of the pulse wave signal and the second time derivative 68" of the pulse wave signal.

This additional information allows potential conclusions to be drawn on changes in the afterload and/or sympathetic activity. A variable quantifying the afterload or a variable quantifying the sympathetic activity may be, for example, the ratio of the duration of the late systole to the duration of the early systole, the ratio of the duration of the late systole to the total duration of the early systole and the late systole, and/or the ratio of the duration of the late systole to the heart rate. Other ratios or other variables derived from the duration of the early systole, the duration of the late systole and/or the heart rate can also be used to obtain quantitative information about a change in afterload and/or sympathetic activity.

The evaluation steps described with reference to FIG. 1 to FIG. 6 for determining the pulse transit time and obtaining additional information on the basis of the pulse wave form can be performed for each heartbeat of a sequence of heartbeats during a relaxation exercise. This may include the detection and evaluation of the pulse wave form as well as the pulse transit time over a period of at least one minute, at least five minutes, at least ten minutes or at least 15 minutes. Biofeedback which depends on the pulse transit time and the evaluation of the pulse wave form can be output during the relaxation exercise and updated from heartbeat to heartbeat.

The pulse transit time and optionally the heart rate can be further processed in order to generate biofeedback. For example, time averaging over a predetermined period of time, which can be at least one minute, can be performed to output the time averages of the pulse transit time and optionally the heart rate as biofeedback. Alternatively or additionally, the energy of the pulse wave signal, the ECG signal or signals derived therefrom can be determined in different frequency ranges. To this end, the pulse wave signal and/or the ECG signal can be subjected to a Fourier transformation and the spectral weight for at least two different frequency bands can be determined on the basis of the signal transformed into the Fourier space, as is described in more detail with reference to FIG. 14. By means of this evaluation of the pulse wave form and the pulse transit time, which indirectly indicates changes in blood pressure, the apparatus 10 allows the respective change in blood pressure to be individually output directly to the user during a relaxation exercise via visual and/or acoustic signals. This offers improvements over traditional methods of biofeedback, which are based, for example, solely on heart rate variability or conventional measurement of the pulse transit time.

Figure 7:
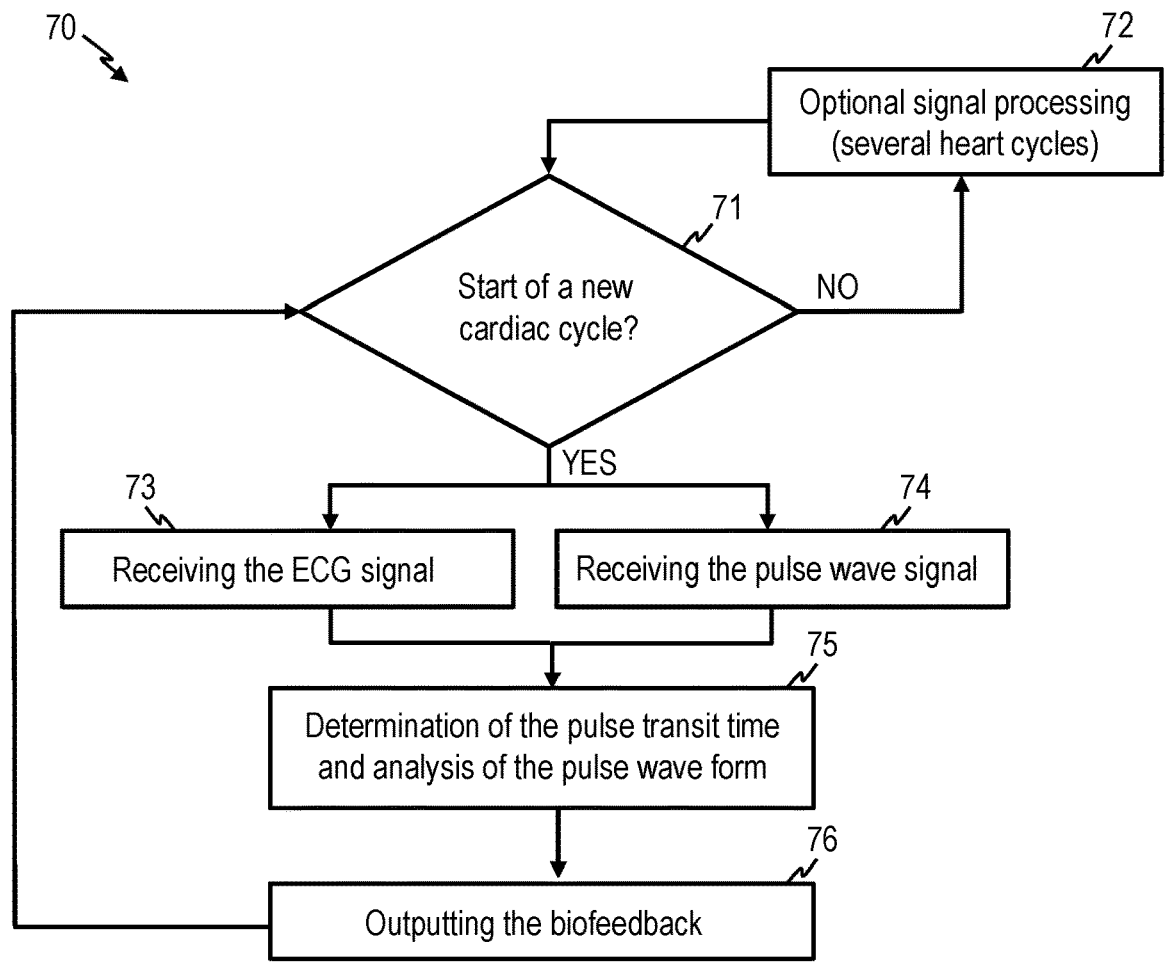
FIG. 7 shows a flow chart of a method according to an exemplary embodiment.

FIG. 7 is a flow chart of a method 70, which can be carried out by the apparatus 10 according to an exemplary embodiment. In this method, the pulse transit time can be determined for each heartbeat of a sequence of heartbeats on the basis of an ECG signal and a pulse wave signal, which represents a pressure pulse or volume pulse in a blood circulation system, and, additionally, the pulse wave form of the pulse wave signal can be evaluated. In this method, it is possible to check at step 71 whether a new cardiac cycle begins. At steps 73 and 74, the ECG signal and the pulse wave signal can be received at at least one interface by sensors 21, 22. The pulse transit time can be determined at step 75. To this end, the time interval between an R wave of the ECG signal and the point in time at which the rising edge of the pulse wave signal begins can be determined. The determination of the pulse transit time can be carried out as described with reference to FIG. 2. At step 75, the pulse wave form can also be analyzed. To this end, it can be determined how the pulse wave form of the pulse wave signal which is detected during the execution of a relaxation exercise changes in comparison to the pulse wave form of at least one preceding pulse wave signal. The pulse wave form of the pulse wave signal detected during a relaxation exercise can be analyzed by comparing the pulse wave form to the pulse wave form of a reference pulse wave signal detected, for example, at the beginning of the relaxation exercise. In order to be able to detect changes in the pulse wave form reliably and easily even when the heart rate changes, the pulse wave signal can be scaled along the time axis, wherein the different durations of the pulse wave signals detected at different times are taken into account in this scaling operation. The analysis of the pulse wave form may include a comparison of the signal strength of the pulse wave signal, especially at one or more local maxima. This allows conclusions to be drawn about the cardiac pumping capacity. The analysis of the pulse wave form may include a comparison of a second peak of the pulse wave form caused by a reflection of the pressure pulse or volume pulse in the peripheral vessels with a corresponding second peak in the pulse wave form of a reference pulse wave signal. Depending on whether the pulse wave form significantly changes in the late systole, it can be determined whether a change in blood pressure is caused by the sympathetic nervous system or the vagus. The biofeedback can be output at step 76. The biofeedback can indicate the change in one or more vital signs during a relaxation exercise as a function of time and/or as a function of a parameter characterizing the performance of the relaxation exercise, such as a breathing rate. The biofeedback may include, but is not limited to, information about a change in blood pressure, a cardiac pumping capacity, a pulse wave reflection and/or a mode of action underlying the change in blood pressure. Optionally, instructions for performing the relaxation exercise can also be output. The instructions can be generated depending on the pulse transit time and/or the analysis of the pulse wave form. The biofeedback can be updated from heartbeat to heartbeat. To this end, the method can return to step 71. Parallel to steps 73-76 or until the start of a new cardiac cycle, various additional processing steps can be performed at step 72. For example, moving averages of the pulse transit time can be calculated and made available to the user as biofeedback.

Figure 8:
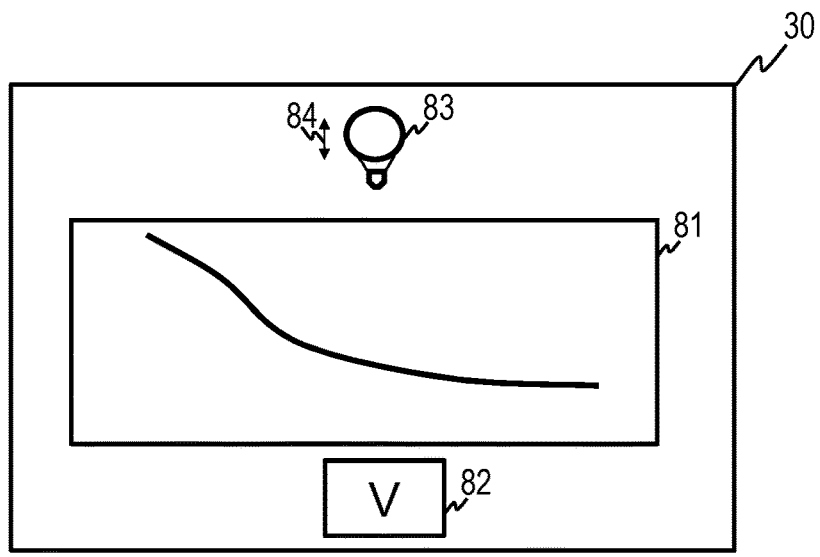
FIG. 8 shows a schematic illustration of an optical output unit for providing biofeedback for an apparatus according to an exemplary embodiment.

FIG. 8 is a schematic illustration of a graphic which is output via an optical output unit 30 and can be generated by the apparatus 10. The apparatus 10 can control the optical output unit 30 to output a graphical representation 81 of a change in blood pressure. The graphical representation 81 may include the change of the pulse transit time during the relaxation exercise. The change in blood pressure can be represented via the pulse transit time as a function of time or as a function of a parameter of the relaxation exercise. The apparatus 10 can control the optical output unit 30 to output additional or alternative information 82 as biofeedback, said information 82 depending on the analysis of the pulse wave form. The additional information may include information about a cardiac pumping capacity, a pulse wave reflection and/or a mode of action underlying the change in blood pressure. The apparatus 10 can optionally control the optical output unit 30 to output instructions for performing the breathing exercise. For example, a graphic symbol 83 can be output to cause the user to breathe in the rhythm of a movement 84 of symbol 83. Alternatively or additionally, the apparatus 10 can also output the instructions via an acoustic output interface, such as a loudspeaker.

Figure 9:
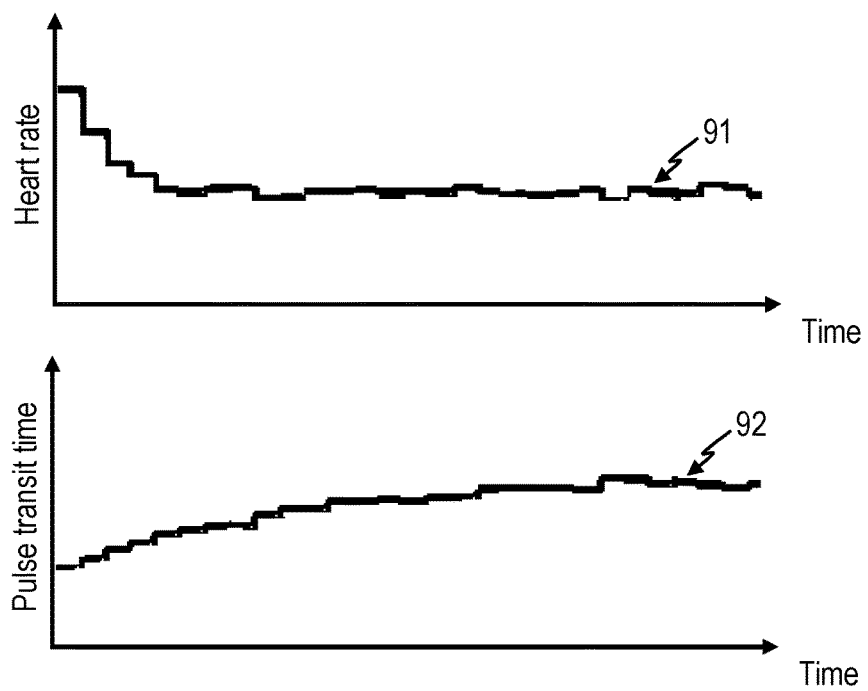
FIG. 9 shows a change in heart rate and pulse transit time during a relaxation exercise.

FIG. 9 shows the change in a heart rate 91 and the change in a pulse transit time 92 during a relaxation exercise, averaged over several subjects. As illustrated by FIG. 9, the heart rate 91 significantly drops to a lower value within a relatively short period of a few minutes after the start of the relaxation exercise and then maintains this value. However, the change in blood pressure, which is reflected in the determined change in pulse transit time 92, only subsides significantly after the point in time at which the heart rate has already adjusted to a lower value. FIG. 9 illustrates that the heart rate and pulse transit time have different time dependencies and that therefore a determination of the pulse transit time as well as an analysis of the pulse wave form are useful for the user.

Figure 10:
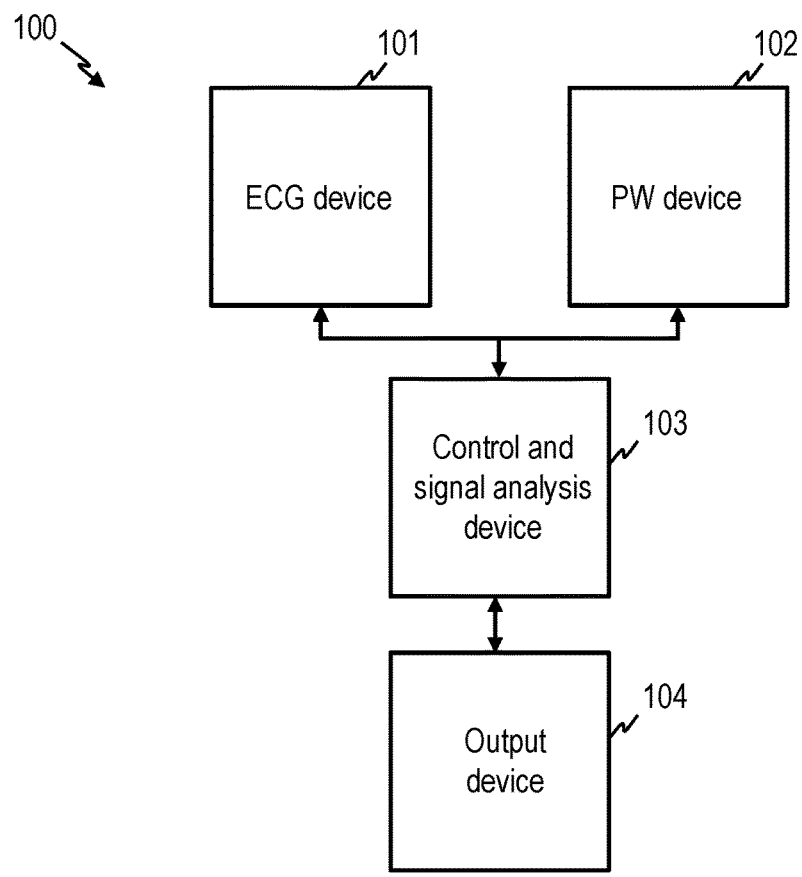
FIG. 10 shows a block diagram of a system according to an exemplary embodiment.

FIG. 10 is a schematic block diagram of a system 100 according to an exemplary embodiment. The system 100 comprises an ECG device 101 for detecting the ECG signal, a device 102 for detecting the pulse wave signal, a control and signal analysis device 103 and an output interface 104. The control and signal analysis device 103 may be integrated into a handheld device such as a cell phone, tablet computer or portable computer.

The control and signal analysis device 103 can control, on the one hand, the interaction with the operator and, on the other hand, the coordination of the signal and data flows within the system 100. The control and signal analysis device 103 can define the interfaces to the sensors as well as the process flows for signal processing. The necessary calculations allowing conclusions to be drawn for central parameters on the basis of peripherally measured data are performed in the control and signal analysis device 103. The control and signal analysis device 103 may be configured to control and synchronize all internal processes and the various data interfaces.

Via an optical and/or acoustic output interface 104, the control and signal analysis device 103 can provide the user with an individually adjusted instruction for carrying out the relaxation exercise, e.g., a timing for breathing. In the case of mantra breathing, this timing can begin with, for example, ten breaths per minute and can then be slowly adjusted downwards to six breaths per minute over the next few weeks. Via the optical and/or acoustic output interface, a continuous record of the pulse transit time, which depends on the blood pressure, as well as the change in pulse transit time depending on the breathing rate can be output. A drop in blood pressure and thus an increase in the pulse transit time can be output to the user via a color coding or by means of a respective acoustic signal.

The measurement of the pulse transit time can be performed continuously via an (ECG) R wave triggered photoplethysmographic measurement, for example on the finger. The system and measurement control is advantageously performed online, since the control is critical in terms of time due to the transient nature of the cardiovascular system. The open-loop and/or closed-loop control operations performed by the control and signal analysis device 103 can be triggered via the ECG signal since, on the one hand, it marks the recurring starting point of the cardiovascular circulation and, on the other hand, can be robustly taken via one or more channels, for example up to six channels.

Since signal processing is critical in terms of time and memory, the periodicity can be exploited and a recursive information window for synchronizing all signals can be defined. This information window can be dependent on the natural frequency of the cardiovascular system, the information propagation and the distances to be covered in the system. The natural frequencies of the human cardiovascular system are typically between 0.5 Hz and 3.5 Hz, depending on the activation state. This is the starting point of the transient behavior of the system. During the relaxation exercise, the natural frequency may change in a cascade-like manner. The wave propagation velocity also changes in connection with the activation of the sympathetic or parasympathetic nervous system and typically ranges between 4 m/s and 30 m/s. The maximum wavelength is determined by the height of the respective person. Thus, the observation window, through which changes are detected and mathematically further processed, depends on several parameters which can be entered in a user-defined way or automatically estimated by the apparatus according to the invention in order to set the observation window in such a way that erasure can be avoided and consistent information retrieval can be ensured. Cascading may result from the different recording locations and the different information propagation of the pulse wave, which may depend on the anatomy and circulatory state of the subject.

In addition to the determination of the pulse transit time, the ECG device 101 also allows the heart rate and/or the heart rate variability to be detected as parameter of the vegetative balance.

Figure 11:
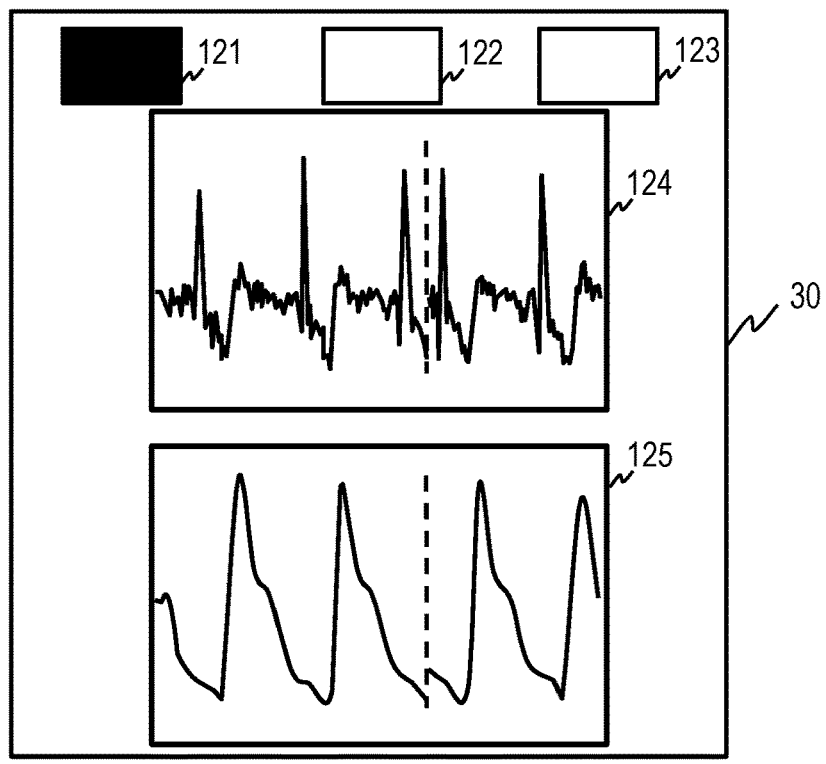
FIG. 11 shows a schematic illustration of an optical output unit for providing biofeedback for an apparatus according to an exemplary embodiment.
Figure 12:
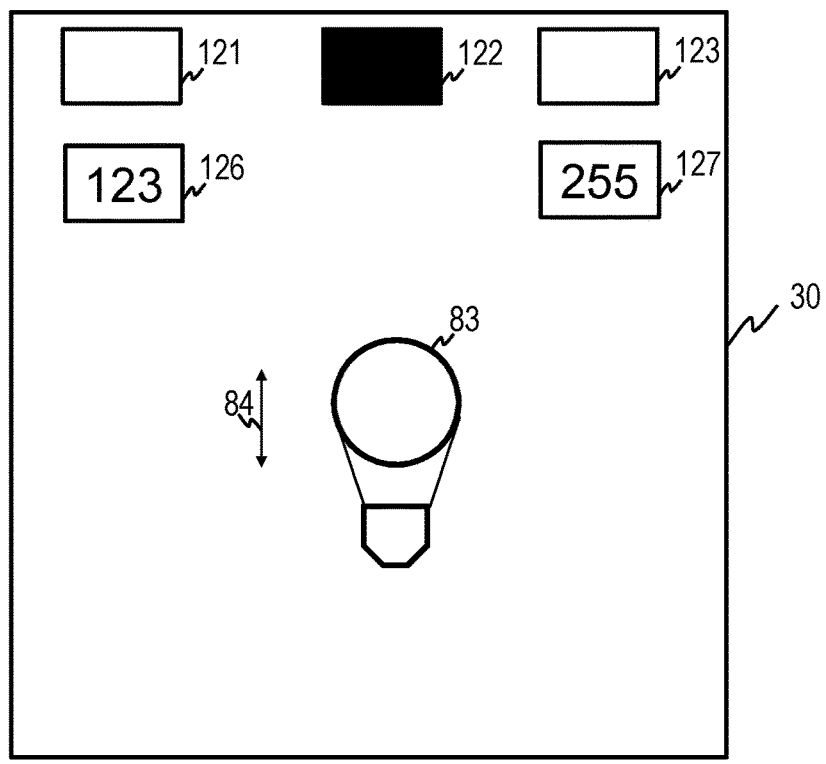
FIG. 12 shows a further schematic illustration of the optical output unit according to FIG. 11.
Figure 13:
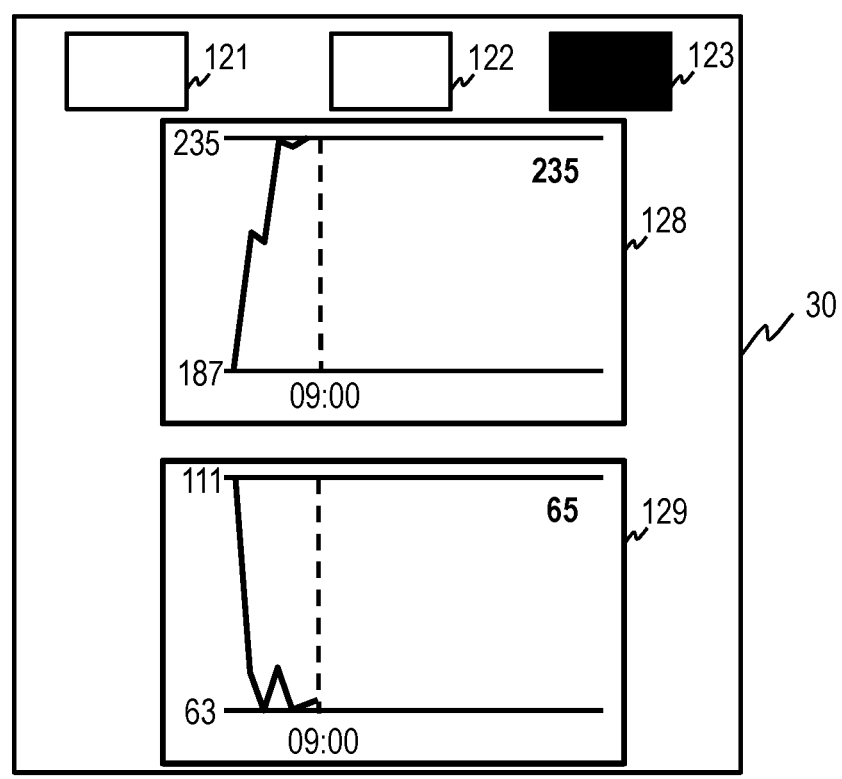
FIG. 13 shows a further schematic illustration of the optical output unit according to FIG. 11.

FIG. 11, FIG. 12 and FIG. 13 respectively show a schematic illustration of a graphic which is output via an optical output unit 30 and can be generated by the apparatus 10. The apparatus 10 can control the optical output unit 30 to provide a plurality of activatable control panels 121-123.

The apparatus can output a raw signal 124 from the first sensor and/or another raw signal 125 from the second sensor in response to a user activity, such as a selection of a control panel 121. The raw signal 124 may be the output signal of an ECG sensor. The further raw signal 125 may be the output signal of a photoplethysmography (PPG) module or another sensor suitable for transit time measurement. The output of the raw signals 124, 125 allows the user to easily check whether the sensors are correctly attached to the body and/or whether the connection for transmitting the output signals has been established. The apparatus can also automatically perform a plausibility check on the basis of the raw signals 124, 125 to determine whether the sensors are correctly attached and the connection of the sensors to the apparatus is correctly established for the signal transmission.

The apparatus can issue instructions for performing the breathing exercise in response to a user activity, such as a selection of a further control panel 122. For example, a graphic symbol 83 can be output to cause the user to breathe in the rhythm of a movement 84 of the symbol 83. Alternatively or additionally, the apparatus 10 can also output the instructions via an acoustic output interface, such as a loudspeaker. Biofeedback can be provided at the same time. For example, a base value 126 of the pulse transit time corresponding to the pulse transit time at the beginning of the exercise and a current value 127 of the pulse transit time can be displayed.

In response to a user activity, such as the selection of a further control panel 123, the apparatus can output a graphical representation 128 of a change in pulse transit time caused by a change in blood pressure. The graphical representation 128 may include the change in pulse transit time during the relaxation exercise and optionally the current value of the pulse transit time. The change in blood pressure can be represented via the pulse transit time as a function of time or as a function of a parameter of the relaxation exercise. The optical output unit 30 can be controlled to output additional information 129 as biofeedback, said additional information 129 depending on the analysis of the pulse wave form and/or the ECG signal. The additional information 129 may represent, for example, the heart rate as a function of time during the relaxation exercise.

In addition or as an alternative to generating biofeedback during a relaxation exercise, the apparatuses and systems may be configured according to exemplary embodiments to generate reports that depend on data detected and evaluated in a plurality of relaxation exercises. For example, the apparatus may be configured to determine in each of a plurality of relaxation exercises whether a change in afterload has been achieved. The change in afterload or any other variable quantifying the resistance of peripheral vessels can be stored in a non-volatile manner for each of the plurality of relaxation exercises. The corresponding variables can be determined by an analysis of the pulse wave form, as described above. When generating a report after a relatively large number of relaxation exercises performed over a period of several days or weeks, the apparatus 10 can generate information indicating whether the subject has succeeded in achieving a reduction in the resistance of peripheral vessels.

Figure 14:
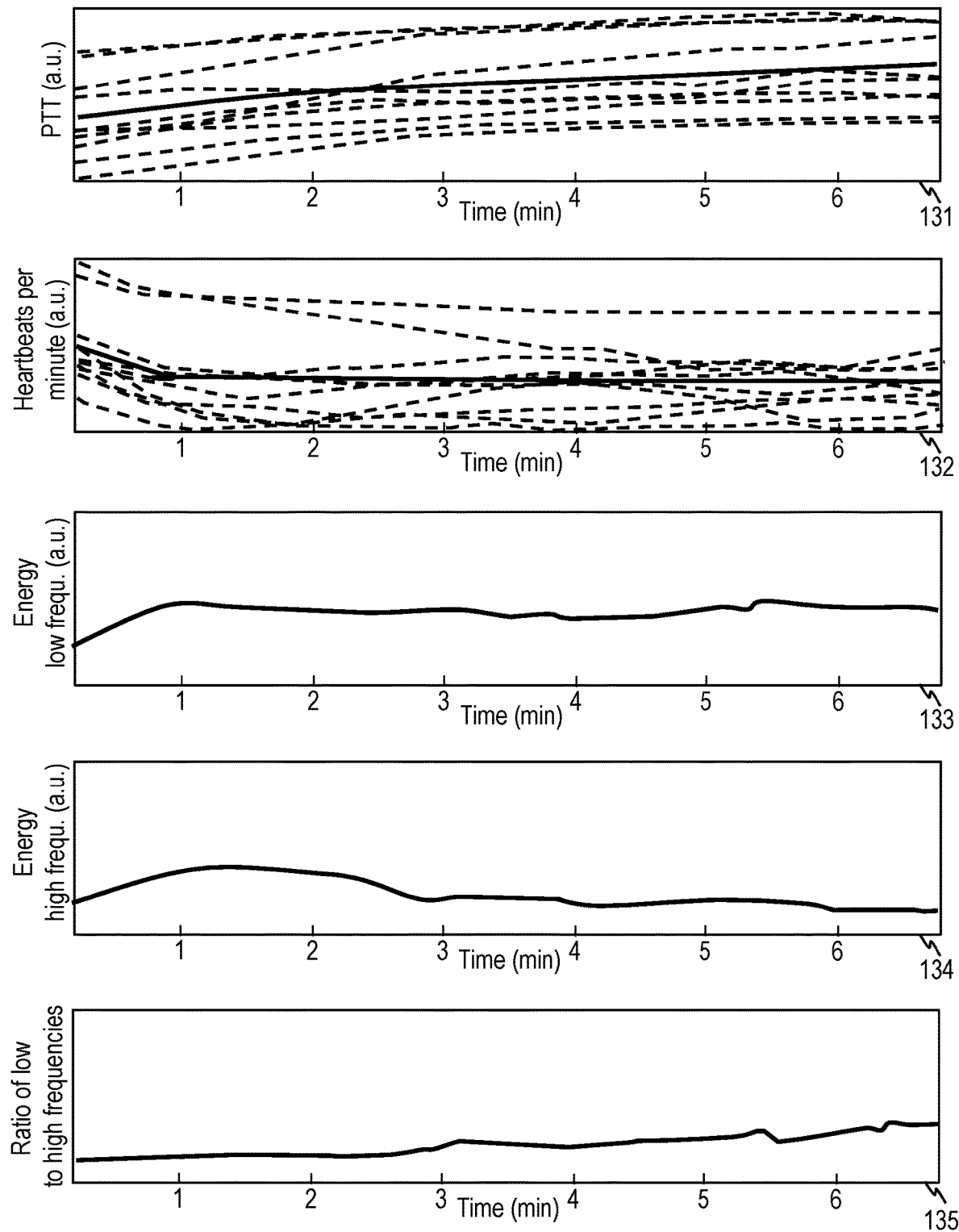
FIG. 14 shows an illustration for explaining techniques to generate biofeedback.

FIG. 14 exemplarily shows pieces of information that can be output individually or in combination by the apparatus 10 as biofeedback. The apparatus 10 can determine a time average of the pulse transit time 131. The apparatus can average the pulse transit time determined from heartbeat to heartbeat over a predetermined time interval, which may be at least one minute, for example. In FIG. 14, the graph for the time average of the pulse transit time 131 shows the respective averages of the pulse transit time determined for each individual exercise with broken lines. The average determined by averaging over various exercises is depicted with a solid line.

The apparatus 10 can optionally also determine a time average of the heart rate 132. The apparatus 10 can average the heart rate determined from heartbeat to heartbeat over a predetermined time interval, which may be at least one minute, for example. In FIG. 14, the graph for the time average of the heart rate 132 shows the respective averages of the heart rate determined for each individual exercise with broken lines. The average determined by averaging over various exercises is depicted with a solid line.

The apparatus 10 can also use more complex processing techniques. For example, the apparatus 10 may be configured to determine the energy of the pulse wave signal and/or the ECG signal in one, two or more than two frequency bands that are different from each other. To this end, the apparatus 10 can, for example, subject the respective signal to a Fourier transformation. The apparatus 10 can numerically integrate the pulse wave signal and/or ECG signal Fourier transformed into the frequency space over the corresponding frequency band to determine the energy in a frequency band. Other techniques may be used to determine the energy of the pulse wave signal, the ECG signal or signals derived therefrom in one, two or more than two frequency bands that are different from each other.

As illustrated in FIG. 14, the apparatus 10 can determine the energy 133 of the pulse wave signal and/or ECG signal in a first frequency band and the energy 134 of the pulse wave signal and/or ECG signal in a second frequency band. The first frequency band may be a frequency interval ($f_{11}$, $f_{12}$), and the second frequency band may be a frequency interval ($f_{21}$, $f_{22}$), wherein $f_{11}<f_{12}<f_{21}<f_{22}$. The apparatus 10 can determine whether the energy 133 in the first frequency band, i.e., at lower frequencies, increases during the relaxation exercise, and/or whether the energy 134 in the second frequency band, i.e., at higher frequencies, decreases during the relaxation exercise. Accordingly, the energy 133, 134 may be used and output as biofeedback in at least one frequency band. Alternatively or additionally, a ratio 135 of the energy 133 in the first frequency band to the energy 134 in the second frequency band can be determined by the apparatus 10.

The apparatus 10 may also be configured to generate alternative or additional processing techniques for generating biofeedback depending on the pulse transit time and/or pulse wave form of pulse waves.

Figure 15:
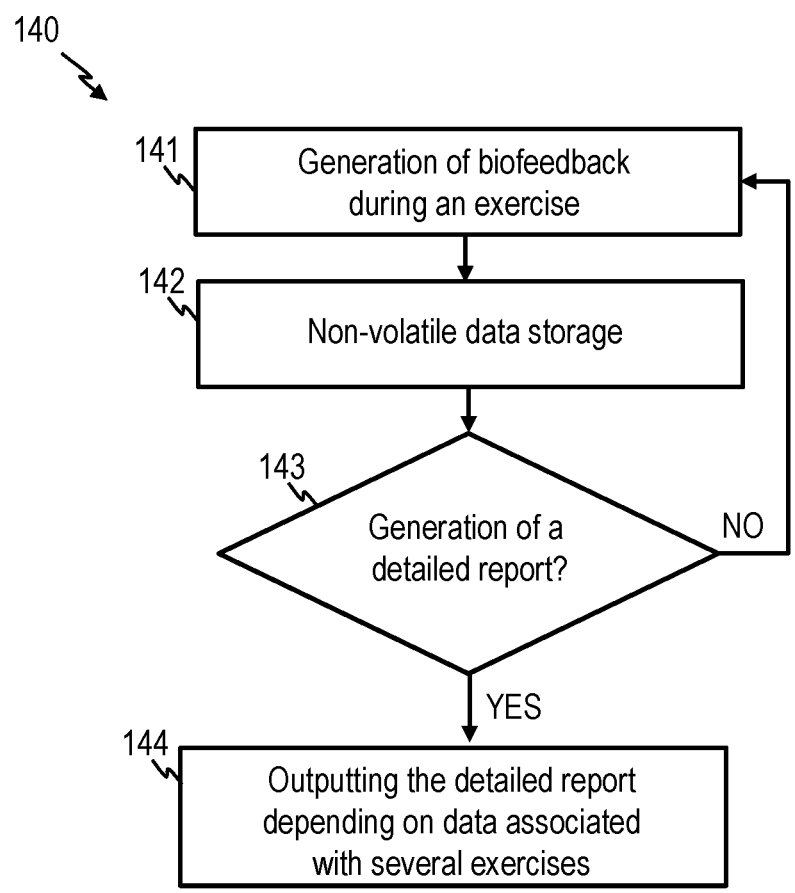
FIG. 15 shows a flow chart of a method according to an exemplary embodiment.

FIG. 15 is a flow chart 140 of a method according to an exemplary embodiment. Biofeedback is generated during a relaxation exercise at step 141. The biofeedback generated during the relaxation exercise may depend on the pulse transit time and optionally on the heart rate and/or an analysis of the pulse wave form of the pulse wave signal. At step 142, data associated with the relaxation exercise can be stored in a non-volatile manner. The data stored in a non-volatile manner can be generated depending on the analysis of the pulse wave form during the relaxation exercise. The data stored in a non-volatile manner may comprise quantitative information about an afterload change or other quantitative information that depends on the resistance of peripheral blood vessels. At step 143, it can be checked whether a detailed report should be generated for being output to the subject and/or a specialist taking care of the subject. A detailed report can be generated, for example, when a predefined number of relaxation exercises has been performed using the apparatus. Alternatively or additionally, a detailed report can be generated if relaxation exercises using the apparatus have been performed over a predefined period of time. Alternatively or additionally, a detailed report can be generated if the subject or a specialist taking care of the subject requests it by user input at the apparatus. If a detailed report is to be generated, it is output via an interface at step 144. The output of the detailed report may include the output of information which has been generated depending on the analysis of the pulse wave form and which indicates whether the subject has succeeded in achieving a reduction in the resistance of peripheral vessels. For example, the change in afterload can be determined and evaluated over several relaxation exercises.

The user may attach both the ECG sensor, which may be configured, for example, as a single-channel ECG sensor, and the photoplethysmographic module to, for example, the finger to use the systems 1, 100. The ECG signal and the pulse wave signal are detected. The pulse transit time is continuously determined on the basis of the offset.

At the beginning of a breathing exercise, for example, the user may breathe with a normal breathing rhythm of ten to twelve breaths per minute. The apparatus 10 can guide the relaxation exercise such that the timing is slowly shifted towards lower breathing rates until, for example, a frequency of six breaths per minute is reached. The blood pressure is lowered by the relaxation exercise, wherein biofeedback is provided to the user. The breathing rate and biofeedback can be communicated via audio and/or visual signals.

The apparatus may be used, for example, for domestic relaxation exercises, the duration of which may be ten to twenty minutes a day and at least sixty minutes a week cumulatively. A reduction in blood pressure with effect sizes of approximately 5 mmHg can be achieved after one to two months, for example.

While exemplary embodiments were described with reference to the Figures, modifications may be realized in further exemplary embodiments. While the apparatuses, systems and methods can provide biofeedback without using a cuff-type blood pressure meter, the apparatuses, systems and methods may also be used with such a cuff-type blood pressure meter. For example, with the use of the cuff-type blood pressure meter before the start of a relaxation exercise or only at the start of a relaxation exercise, a calibration can be performed in such a way that the pulse transit time can be related to an absolute value of the blood pressure. This enables the output not only of relative changes in blood pressure during the relaxation exercise, but optionally also of absolute values of the blood pressure.

While exemplary embodiments were described with reference to the generation of biofeedback during guided breathing exercises, such as mantra breathing, the apparatuses, systems and methods for generating biofeedback may also be used in other relaxation exercises.

Apparatuses, systems and methods according to exemplary embodiments can use the ECG signal not only to determine the pulse transit time. Apparatuses, systems and methods according to exemplary embodiments can use the ECG signal both to determine the pulse transit time and to determine the heart rate variability. The heart rate variability can be output as biofeedback, for example, in addition to the change in pulse transit time. Apparatuses, systems and methods according to exemplary embodiments may be used to provide biofeedback, especially in relaxation exercises for lowering blood pressure in mild hypertension, without being limited thereto.

The invention claimed is:

1. An apparatus for generating biofeedback, comprising:
at least one interface for receiving a pulse wave signal, which represents a pressure pulse or volume pulse of a pulse wave in a blood circulation system as a function of time, and an ECG signal, the at least one interface being configured to synchronize data transmission and data acquisition between sensors that capture the pulse wave signal and the ECG signal,
an evaluation device comprising an integrated semiconductor circuit that is configured to determine a pulse transit time on a basis of the pulse wave signal and the ECG signal, perform an evaluation of a pulse wave form of the pulse wave signal and generate the biofeedback depending on the pulse transit time and/or the evaluation of the pulse wave form, wherein the integrated semiconductor circuit of the evaluation device is configured to determine whether there is a change in blood pressure caused by vagus enhancement or sympathetic attenuation by comparison of the pulse wave form with a reference pulse wave form, and
an output interface for providing the biofeedback and to indicate via the output interface whether there is a change in blood pressure caused by vagus enhancement or sympathetic attenuation which improves vegetative balance of a user of the apparatus, wherein the output interface is configured to output both the biofeedback and instructions for performing a relaxation exercise, wherein the instructions for performing the relaxation exercise are generated by the apparatus using a value of an adjustable parameter that depends on the pulse transit time and/or the evaluation of the pulse wave form.

2. The apparatus according to claim 1, wherein the evaluation device is configured to determine a mode of action underlying the change in blood pressure, a magnitude of the change in blood pressure and/or a change in pulse wave reflection by evaluating the pulse wave form.

3. The apparatus according to claim 1, wherein the evaluation device is configured to determine a change in afterload by evaluating the pulse wave form.

4. The apparatus according to claim 3, wherein the evaluation device is configured to output the change in afterload via the output interface.

5. The apparatus according to claim 3, wherein the evaluation device is configured to detect a change in at least one of the following variables in order to determine whether there is the change in blood pressure caused by vagus enhancement or sympathetic attenuation:
duration of an early systolic phase;
pressure in the early systolic phase; or
duration of a late systolic phase.

6. The apparatus according to claim 1, wherein the evaluation device is configured to determine a change in cardiac pumping capacity by evaluating the pulse wave form.

7. The apparatus according to claim 1, wherein the evaluation device is configured to perform the respective determination of the pulse transit time and/or the respective evaluation of the pulse wave form for each cardiac cycle of a plurality of successive cardiac cycles.

8. The apparatus according to claim 7, wherein the apparatus is configured to output the respective biofeedback via the output interface for each cardiac cycle of the plurality of successive cardiac cycles.

9. The apparatus according to claim 1, wherein the biofeedback comprises at least one piece of information selected from the group consisting of: the change in blood pressure, blood pressure, cardiac pumping capacity, change in afterload, pulse wave reflection, or mode of action underlying the change in blood pressure.

10. The apparatus according to claim 1, wherein the output interface comprises an optical output unit, wherein the apparatus is configured to output the instructions for performing the relaxation exercise and the biofeedback at the same time via the optical output unit.

11. The apparatus according to claim 1, wherein the evaluation device is configured to determine the pulse transit time and/or at least one characteristic of the pulse wave form determined by the evaluation of the pulse wave form as a function of a parameter of the relaxation exercise.

12. The apparatus according to claim 1, wherein the apparatus is configured for generating the biofeedback during the relaxation exercise for lowering the blood pressure.

13. A system, comprising:
an apparatus for generating biofeedback, the apparatus comprising
at least one interface for receiving a pulse wave signal, which represents a pressure pulse or volume pulse of a pulse wave in a blood circulation system as a function of time, and an ECG signal, the at least one interface being configured to synchronize data transmission and data acquisition between the pulse wave signal and the ECG signal,
an evaluation device comprising an integrated semiconductor circuit that is configured to determine a pulse transit time on a basis of the pulse wave signal and the ECG signal, perform an evaluation of a pulse wave form of the pulse wave signal and generate the biofeedback depending on the pulse transit time and/or the evaluation of the pulse wave form, wherein the evaluation device is configured to determine whether there is a change in blood pressure caused by vagus enhancement or sympathetic attenuation by comparison of the pulse wave form with a reference pulse wave form, and
an output interface for providing the biofeedback and to indicate via the output interface whether there is a change in blood pressure caused by vagus enhancement or sympathetic attenuation which improves vegetative balance of a user of the apparatus, wherein the output interface is configured to output both the biofeedback and instructions for performing a relaxation exercise, wherein the instructions for performing the relaxation exercise are generated by the apparatus using a value of an adjustable parameter that depends on the pulse transit time and/or the evaluation of the pulse wave form; and a sensor device which is couplable to said at least one interface of the apparatus and configured to detect the pulse wave signal and the ECG signal.

14. The system according to claim 13, wherein the sensor device comprises a first sensor for detecting the pulse wave signal and a second sensor for detecting the ECG signal.

15. The system according to claim 13, wherein the apparatus is configured for generating the biofeedback during the relaxation exercise for lowering the blood pressure.

16. A method for generating biofeedback, comprising the steps of:

receiving, by an apparatus, a pulse wave signal, which represents a pressure pulse or volume pulse of a pulse wave in a blood circulation system as a function of time, and an ECG signal by at least one interface, the at least one interface being configured to synchronize data transmission and data acquisition between sensors that capture the pulse wave signal and the ECG signal, determining, by the apparatus, a pulse transit time by evaluating the pulse wave signal and the ECG signal, evaluating, by the apparatus, a pulse wave form of the pulse wave signal to determine whether there is a change in blood pressure caused by vagus enhancement or sympathetic attenuation by comparison of the pulse wave form with a reference pulse wave form, generating, by the apparatus, the biofeedback depending on the pulse transit time and/or the evaluation of the pulse wave form, and outputting, by the apparatus, the biofeedback and instructions for performing a relaxation exercise and indicating via an output interface whether there is a change in blood pressure caused by vagus enhancement or sympathetic attenuation which improves vegetative balance of a user of the apparatus, wherein the instructions for performing the relaxation exercise are generated by the apparatus using a value of an adjustable parameter that depends on the pulse transit time and/or the evaluation of the pulse wave form.

17. The method according to claim 16, wherein the biofeedback is generated during the relaxation exercise for lowering the blood pressure.

18. The method according to claim 17, wherein the relaxation exercise comprises a breathing exercise.

19. The method according to claim 16, wherein the ECG signal is used both to determine the pulse transit time and to determine a heart rate variability.

20. The method according to claim 16, which is carried out by the apparatus for generating the biofeedback, the apparatus comprising:

the at least one interface for receiving the pulse wave signal that represents the pressure pulse or volume pulse of the pulse wave in the blood circulation system as the function of time and the ECG signal;

an evaluation device that is configured to determine the pulse transit time on the basis of the pulse wave signal and the ECG signal, perform the evaluation of the pulse wave form of the pulse wave signal and generate the biofeedback depending on the pulse transit time and/or the evaluation of the pulse wave form; and the output interface for providing the biofeedback.

* * * * *